(12) United States Patent
Appéré

(10) Patent No.: US 6,613,919 B2
(45) Date of Patent: Sep. 2, 2003

(54) METHOD FOR RESOLVING RACEMIC MIXTURES OF 5-SUBSTITUTED 4-HYDROXY-2-FURANONES

(75) Inventor: Georges Appéré, Sucy en Brie (FR)

(73) Assignee: Oxis Isle of Man, Portland, OR (US)

( * ) Notice: Subject to any disclaimer, the term of this patent is extended or adjusted under 35 U.S.C. 154(b) by 0 days.

(21) Appl. No.: 10/184,797

(22) Filed: Jun. 28, 2002

(65) Prior Publication Data

US 2003/0065196 A1 Apr. 3, 2003

Related U.S. Application Data

(63) Continuation of application No. PCT/IB99/02068, filed on Dec. 29, 1999.

(51) Int. Cl.$^7$ ............................................. C07D 307/62
(52) U.S. Cl. ........................................ 549/315; 203/48
(58) Field of Search ............................ 549/315; 203/48

(56) References Cited

U.S. PATENT DOCUMENTS

| 3,541,139 A | 11/1970 | Winterbottom et al. |
| 4,005,088 A | 1/1977 | Gubbels et al. |

FOREIGN PATENT DOCUMENTS

| FR | 2 259 073 | 8/1975 |
| GB | 565474 | 12/1942 |
| GB | 605444 | 10/1944 |
| GB | 773174 | 8/1955 |
| JP | 07285955 | 10/1995 |
| WO | WO 97/11927 | 4/1997 |
| WO | WO 98/07714 | 2/1998 |

OTHER PUBLICATIONS

Jacques et al, US, Malabar, Krieger, 253–259 (1991) (Abstract).
Chemical Abstracts, vol. 121, No. 18, (1994) Columbus, Ohio, US, Abstract No. 220654; and Wongyai: Chromatographia, 38:609–612 (1994).
Chemical Abstracts, vol. 86, No. 21, (1977) Columbus, Ohio, Abstract No. 155897; and JP 51 108061A, Asahi Chemical Industry Co., Ltd.
Database WPI Week 199716, Derwent Publications Ltd., London, GB; JP09 040667 A, Mitsui Toatsu Chem. Inc. (1997) (Abstract).

*Primary Examiner*—Taofiq Solola
(74) *Attorney, Agent, or Firm*—Klauber & Jackson

(57) ABSTRACT

This invention affords a solution to the technical problem of obtaining one or both enantiomers of 5-substituted 4-hydroxyfuran-2-ones in pure form by resolution with enantiomerically pure bases. Racemic mixtures of 5-substituted 4-hydroxy-2(5H)-furanones, including 5-substituted and 5,5-disubstituted, 4-hydroxy and 3,4-dihydroxy furanones are separated into pure enantiomers by crystallization with an enantiomerically pure base, such as cinchonidine. In specific solvent mixtures, for example, 95% ethanol, the diastereomerically pure salt of one enantiomer crystallizes. The enantiomerically pure furanone can then be obtained simply by filtration and treatment of the salt with an acid, for example, trifluoracetic acid, followed by precipitation with water, filtration and drying. Moreover, the other enantiomer may be equally obtained in pure form by evaporation of the mother liquor, followed by the same treatment of the salt as described before.

15 Claims, No Drawings

METHOD FOR RESOLVING RACEMIC MIXTURES OF 5-SUBSTITUTED 4-HYDROXY-2-FURANONES

This application is a continuation of PCT/IB99/02068 filed Dec. 29, 1999.

FIELD OF THE INVENTION

This invention provides a method for isolation of one or both enantiomers of 5-substituted or 5,5-disubstituted 4-hydroxy-2-furanones or 3,4-dihydroxy-2-furanones in pure form, by resolution with enantiomerically pure bases.

BACKGROUND OF THE INVENTION

Synthesis of enantiomerically pure compounds is tedious work, and while producing the desired pure compound, often is done by sacrificing yield. Such methods often are not suitable for scale up and the preparation of multi-gram or greater quantities.

Preparation of racemic mixtures of compounds followed by separation or isolation of the desired enantiomers is a more promising approach. Methods for the resolution of racemic mixtures has employed, for example, enantiomers of derivatives of phenoxypropionic acid for the separation of papaverine (WO 97/11927), cinchonidine for the separation of aminocarboxylic acid derivatives (U.S. Pat. No. 4,005,088), or quinine trihydrate for the separation of enantiomers of hydroxyphenylacetic acid derivatives (British Patent Specification 1,241,844).

The enantiomers of 5-substituted or 5,5-disubstituted 4-hydroxy or 3,4-dihydroxy-2(5H)-furanones have numerous therapeutic utilities which take advantage of their anti-inflammatory, anti-lipidemic and anti-aggregatory activities, among others, which are useful in the treatment of numerous conditions and diseases such as cardiovascular disease including atherosclerosis; asthma; rheumatoid arthritis; inflammatory bowel disease; acute respiratory distress syndrome; neurodegenerative disorders such as Alzheimer disease, Parkinson disease, amyotrophic lateral sclerosis, traumatic brain injury, and multiple sclerosis; and viral diseases including AIDS. Such compounds and uses are described in, for example, U.S. Pat. Nos. 5,298,526; 5,399,721; 5,504,108; 5,504,107; 5,656,662; 5,095,126; 5,071,872; WO 98/07714; and U.S. Ser. No. 09/406,544, filed Sep. 27, 1999; all of which are incorporated by reference herein in their entireties. However, methods for the separation of the enantiomers of these compounds from the racemic mixture were not previously known. Asymmetric synthesis of such compounds as described, for example, in U.S. Pat. No. 5,399,721, produces a low yield (5–7%) which is unfeasible for large scale or commercial preparation.

It is towards the process for resolving enantiomers of 5-substituted or 5,5-disubstituted 4-dihydroxy-2(5H)-furanones or 3,4-dihydroxy-2(5H)-furanones in pure form that the present invention is directed.

The citation of any reference herein should not be construed as an admission that such reference is available as "Prior Art" to the instant application.

SUMMARY OF THE INVENTION

This invention affords a solution to the technical problem of obtaining one or both enantiomers of 5-substituted or 5,5-disubstituted 4-hydroxy-2(5H)-furanones or 3,4-dihydroxy-2(5H)-furanones in pure form by resolution with enantiomerically pure bases. In the practice of the invention, the 5-substituted 4-hydroxy-2(5H)-furanone is mixed with an enantiomerically pure chiral base, to form a diastereoisomeric salt. The diastereoisomeric salts may then be separated. For example, in an appropriate solvent, one stereoisomeric salt of one enantiomer precipitates, and thus can be separated, washed, and the enantiomerically pure furanone recovered from the salt by hydrolysis. The other enantiomer may be recovered from the stereoisomeric salt which remains dissolved in the mother liquor. Other means for separation of the salts are embraced herein; selective precipitation of one stereoisomeric salt is preferred.

Non-limiting examples of enantiomerically pure bases useful for the practice of the invention include cinchonidine, cinchonine, quinine, quinidine, brucine, strychnine, α-methylbenzylamine, ephedrine, amphetamine, dehydroabietylamine. Cinchonidine is preferred. Non-limiting examples of solvents include ethanol (anhydrous or aqueous), methanol or other alcohols, acetone (anhydrous or aqueous), ethyl acetate, water, dioxane, mixtures of solvents containing at least one alcohol, and others. A solven of 95% ethanol (aq.) is preferred. The skilled artisan will readily be able to determine an appropriate solvent in which the separation may occur.

The methods of the present invention are not limited to any particular 5-substituted 4-hydroxy-2(5H)-furanones. Additional substitutions are embraced herein. Such compounds include both 5-substituted and 5,5-disubstituted compounds, and include 4-hydroxy-2(5H)-furanones and 3,4-dihydroxy-2(5H)-furanones. 5-Substituted and 5,5-disubstituted 3,4-dihydroxy-2(5H)-furanone are preferred.

Thus, in its broadest aspect, the invention is directed to a method for the separation of a racemic mixture of a 5-substituted 4-hydroxy-2(5H)-furanone, comprising the steps of (a) reacting in a solvent the racemic mixture with an enantiomerically pure base in an amount sufficient to form a diastereoisomeric salt of the 5-substituted 4-hydroxy-2(5H)-furanone; and (b) separating a stereoisomeric salt of one enantiomer of the 5-substituted 4-hydroxy-2(5H)-furanone from the solvent.

A preferred method of separation is by precipitation of one of the stereoisomeric salts.

The invention is further directed to a method for obtaining an enantiomerically pure 5-substituted 4-hydroxy-2(5H)-furanone from a racemic mixture thereof comprising carrying out the separation in accordance with the above steps, separating one stereoisomeric salt of one of the enantiomers of the 5-substituted 4-hydroxy-2(5H)-furanone, and then hydrolyzing the separated stereoisomeric salt of one enantiomer of said 5-substituted 4-hydroxy-2(5H)-furanone to provide the pure 5-substituted 4-hydroxy-2(5H)-furanone.

In another embodiment of the invention, a method is provided for obtaining an enantiomerically pure 5-substituted 4-hydroxy-2(5H)-furanone from a racemic mixture thereof comprising carrying out the separation in accordance with the above steps, separating one stereoisomeric salt of one of the enantiomers of the 5-substituted 4-hydroxy-2(5H)-furanone by selective precipitation, isolating the precipitate, and then hydrolyzing the separated stereoisomeric salt of one enantiomer of said 5-substituted 4-hydroxy-2(5H)-furanone to provide the pure 5-substituted 4-hydroxy-2(5H)-furanone.

In a further aspect of the above procedures, the other stereoisomeric salt which was not separated by the foregoing methods may be recovered from the solvent, and hydrolyzed to provide the other enantiomer. In the instance wherein the separation was performed by precipitation of one of the stereoisomeric salts from the mother liquor, the other stereoisomeric salt may be recovered from the mother liquor, and hydrolyzed to produce the other enantiomer.

In the foregoing methods, the 5-substituted 4-hydroxy-2(5H)-furanone may be, for example, a 5-substituted 4-hydroxy-2(5H)-furanone; a 5,5'-disubstituted 4-hydroxy-2(5H)-furanone; a 5-substituted 3,4-dihydroxy-2(5H)-furanone; or a 5,5-disubstituted 3,4-dihydroxy-2(5H)-furanone.

Enantiomerically pure bases useful for the practice of the present invention include but are not limited to cinchonidine, cinchonine, quinine, quinidine, brucine, strychnine, α-methylbenzylamine, ephedrine, amphetamine, and dehydroabietylamine. These and other aspects of the present invention will be better appreciated by reference to the following Detailed Description.

DETAILED DESCRIPTION OF THE INVENTION

It has been found by the inventor herein that the enantiomers of 5-substituted and 5,5-disubstituted 4-hydroxy-2(5H)-furanones and 3,4-dihydroxy-2(5H)-furanones may be separated from racemic mixtures of the compound by utilizing an enantiomerically pure chiral base to form a diasteromeric salt with the enantiomers of the racemic mixture. The stereoisomeric salt of one of the enantiomers is subsequently separated. As no previous methods for separating enantiomers from racemic mixtures of 5-substituted 4-dihydroxy-2(5H)-furanones were known, and the chemistry of the 5-substituted 4-dihydroxy-2(5H)-furanones is different from that of compounds previously separated using enantiomerically pure chiral bases, as the furanones possess an acidic proton at the chiral center, the finding that the enantiomerically pure chiral bases, first, permit the formation of diastereoisomeric salts of these compounds; secondly, that they could be separated by, for example, selective precipitation; and thirdly, that reisomerization of the enantiomer does not occur upon hydrolysis of the salt is a surprising and unanticipated finding. This method provides means for separation of enantiomers at all scales of preparation, including manufacture.

Furthermore, after separation of one of the stereoisomeric salts from the mother liquor, the remaining stereoisomeric salt may also be isolated, and the enantiomer recovered therefrom by hydrolysis; thus, the methods of the invention provide methods for isolating either or both enantiomers from a racemic mixture. Based on the teachings herein, the relative amounts or ratios of the 5-substituted 4-dihydroxy-2(5H)-furanone and of the enantiomerically pure chiral bases used in the process may be adjusted appropriately depending on whether the object of the process is to maximize recovery and/or purity of the enantiomer which forms the separable diastereomeric salt, maximize recovery and/or purity of the enantiomer which does not form a separable salt and will be left in the mother liquor, or maximize recovery and/or purity of both enantiomers. The skilled artisan will readily be able to adjust these conditions to achieve the desired process.

The separation of the enantiomers herein is based upon different properties between the salt of one of the enantiomers and that of the other. Such differences are well known to one of skill in the art, as such differences are routinely exploited to selectively separate, often by precipitation, a compound from solution, including individual stereoisomeric salts. However, the methods herein are not limited to precipitation, but any method that takes advantage of the differences between the salts. As is known in the art, the conditions to achieve selective precipitation include the composition of the solvent, concentration, temperature, etc. These can be determined routinely by the skilled artisan using the particular compound of which separation of the enantiomers is desired, and the well-known technique of recrystallization. In a non-limiting example, precipitation of one stereoisomeric salt may be achieved using 95% ethanol as the solvent. Other useful solvent that may be used include methanol or other alcohols, acetone (anhydrous or aqueous), ethyl acetate, water, dioxane, mixtures of solvents containing at least one alcohol, and others. The skilled artisan experienced in recrystallization will readily be able to find a suitable solvent.

By way of non-limiting example, the enantiomerically pure chiral base may be that of cinchonidine, cinchonine, quinine, quinidine, brucine, strychnine, α-methylbenzylamine, ephedrine, amphetamine, and dehydroabeitylamine. Cinchonidine is preferred. The amount of enantiomerically pure base used may be from about one-half equivalent of base per equivalent of racemic 5-substituted 4-dihydroxy-2(5H)-furanone, to about one equivalent of base per equivalent of 5-substituted 4-dihydroxy-2(5H)-furanone, although this ratio may be adjusted depending on the particular circumstances of the separation, as described above, and depending on the desired recovery of the enantiomer of the 5-substituted 4-dihydroxy-2(5H)-furanone which does not form a precipitatable diasteromeric salt with the chiral base.

The use of an enantiomerically pure chiral base for the separation of 5-substituted 4-dihydroxy-2(5H)-furanones may be carried out by any of a number of preparative methods known of one of ordinary skill in the art. For example, separation of the enantiomers may be achieved by the steps of (a) mixing in a solvent the racemic 5-substituted 4-hydroxy-2(5H)-furanone with an enantiomerically pure chiral base, to form a diastereomeric salt, where the salt of one enantiomer precipitates from the solvent;

(b) isolating the precipitated diastereomeric salt from the mother liquor; and (c) recovering the enantiomerically pure 5-substituted 4-dihydroxy-2(5H)-furanone from the salt by hydrolysis.

From a chemical preparative perspective, the isolation of a precipitated salt containing one of the desired enantiomers is a straightforward procedure, as the precipitate can be collected, washed free of the mother liquor, and then further processed to recover the enantiomer, for example, by hydrolysis. Of course, additional recrystallization steps may be necessary to increase the purity of the isolated salt from that of the other enantiomer; such additional round(s) of recrystallization is a standard procedure and expected necessity when isolating and purifying precipitates, as the initial purity may not be adequate for the intended use of the product. Such additional means for purifying the particular stereoisomeric salt is embraced in the invention herein.

Methods other than precipitation that may be used to separate the diastereoisomeric salts based on differences in solubility or polarity of the salts, although selective precipitation is the most feasible and preferred method herein.

As noted above, the salt of the enantiomer which does not precipitate remains in the solvent (mother liquor) and can be isolated after the precipitate is separated out. Subsequently, the enantiomer may be obtained from the salt by hydrolysis, in similar fashion to that from the precipitated salt. Of course, this enantiomer or its stereoisomeric salt may need to be recrystallized, possible repeatedly, to obtain the product at the purity needed for the intended use.

Hydrolysis of the separated stereosomeric salts may be achieved by hydrolysis, conditions well known to the chemist. For example, the salt may be treated with acid to generate the free furanone. In an example illustrative of the procedure, the salt is suspended in a solvent and trifluoroacetic acid added dropwise until the salt dissolves. Subsequently, the free furanone may be precipitated by addition of water. Such methods for hydrolysis are well known to the skilled chemist.

As noted above, the term 5-substituted 4-hydroxy-2(5H)-furanones embraces both 5-substituted and 5,5-disubstituted 4-hydroxy- and 3,4-dihydroxy-2(5H)-furanones. The racemic 5-substituted 4-hydroxy-2(5H)-furanones that may be separated by the methods described herein include, but are not limited to, those described in U.S. Pat. Nos. 5,298,526; 5,399,721; 5,504,108; 5,504,107; 5,656,662; 5,095,126; 5,071,872; WO 98/07714; and U.S. Ser. No. 09/406,544, filed Sep. 27, 1999. These citations are merely examples of the types of compounds by which enantiomers may be separated by the methods described herein. Such disclosures include 5-substituted compounds, such as 5-aryl and 5-alkyl derivatives, as well as 5,5-disubstituted compounds. Examples of such compounds include 5-substituted and 5,5-disubstituted-3,4-dihydroxy-2(5H)-furanones of the general formula I

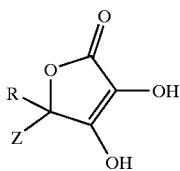

(I)

wherein at least one of Z or R is optionally substituted alkyl or alkenyl group; one may be hydrogen. Examples of such compounds of Formula I include:
3,4-dihydroxy-5-methyl-2(5H)-furanone;
3,4-dihydroxy-5-ethyl-2(5H)-furanone;
3,4-dihydroxy-5-(1-propyl)-2(5H)-furanone;
3,4-dihydroxy-5-(2-propyl)-2(5H)-furanone;
3,4-dihydroxy-5-(1-hexyl)-2(5H)-furanone;
3,4-dihydroxy-5-(3-octadecanyl)-2(5)H-furanone; and
3,4-dihydroxy-5-(3,6,9,12-octadecatetraenyl)-2(5H)-furanone.

Examples of other such compounds include 5-substituted and 5,5-disubstituted-3,4-dihydroxy-2(5H)-furanones of the general formula II

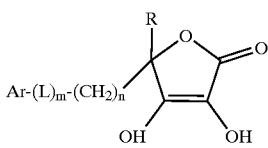

(Formula II)

wherein R is hydrogen, phenyl or lower alkyl; L is a linker moiety selected from the group consisting of oxygen, sulfur, nitrogen, acetylene, a cis or trans carbon—carbon double bond, an ester, carbonate, urea, amide and carbamate; m is 0 or 1; n is 0 to 4; Aryl is a substituted or unsubstituted aryl group; and the pharmaceutically acceptable salts thereof.

Examples of such compounds of Formula II include
3,4-dihydroxy-5-methyl-5-phenyl-2(5H)-furanone;
5-[(1,1'-biphenyl)-4-yl]-3,4-dihydroxy-5-methyl-2(5H)-furanone;
3,4-dihydroxy-5-methyl-5-[4-(2-methylpropyl)phenyl]-2(5H)-furanone;
5-(4-chlorophenyl)-3,4-dihydroxy-5-methyl-2(5H)-furanone;
5-[(1,1'-biphenyl)-4-yl]-3,4-dihydroxy-5-propyl-2(5H)-furanone;
5-[(1,1'-biphenyl)-4-yl]-3,4-dihydroxy-5-(2-methylpropyl)-2(5H)-furanone;
5-[(1,1'-biphenyl)-4-yl]-3,4-dihydroxy-5-phenyl-2(5H)-furanone;
3,4-dihydroxy-5,5-diphenyl-2(5H)-furanone;
3,4-dihydroxy-5-(4-isobutylphenyl)-5-(1-propyl)-2(5H)-furanone;
3,4-dihydroxy-5-(4-isobutylphenyl)-5-phenyl-2(5H)-furanone;
3,4-dihydroxy-5-[2-(4-phenoxy)phenoxyethyl]-2(5H)-furanone;
3,4-dihydroxy-5-[2-(flavone-6-oxy)ethyl]-2(5H)-furanone;
5-[2-(dibenzofuran-2-oxy)ethyl]-3,4-dihydroxy-2(5H)-furanone;
3,4-dihydroxy-5-[2-(1-naphthoxy)ethyl]-2(5H)-furanone;
3,4-dihydroxy-5-[2-(1,8-naphthalimide)-N-ethyl]-2(5H)-furanone;
3,4-dihydroxy-5-[2-(1,8-naphthosultam)-N-ethyl]-2(5H)-furanone;
3,4-dihydroxy-5-[2-(diphenylmethane-2-oxy)ethyl]-2(5H)-furanone;
5-[2-((1,1'-biphenyl)-4-oxy)ethyl]-3,4-dihydroxy-2(5H)-furanone; and
3,4-dihydroxy-5-[2-(quinoline-2-oxy)ethyl]-2(5H)-furanone.

Other compounds include those of the general formula III

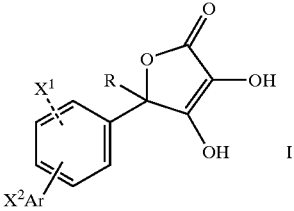

(Formula III)

wherein R is hydrogen, a lower alkyl group optionally substituted by one or more halo groups, a cycloalkyl group, or an aryl group optionally substituted by one or more halo, alkyl of one to eight carbon atoms, alkoxy of one to eight carbon atoms, cycloalkyl, nitro or trifluoromethyl groups; $X^1$ is optionally one or more halo, alkyl of one to eight carbon atoms, alkoxy of one to eight carbon atoms, cycloalkyl, nitro or trifluoromethyl groups; and Ar is an aromatic or heteroaromatic ring substituted by $X^2$, $X^2$ being one or more halo, alkyl of one to eight carbon atoms, alkoxy of one to eight carbon atoms, cycloalkyl, nitro or trifluoromethyl groups; or a pharmaceutically acceptable salt thereof.

Examples of such compounds of Formula III include
5-[(4'-fluoro-1,1'-biphenyl)-4-yl]-5-methyl-3,4-dihydroxy-2(5H)-furanone;
5-[(4'-bromo-1,1'-biphenyl)-4-yl]-5-methyl-3,4-dihydroxy-2(5H)-furanone;
5-[(4'-chloro-1,1'-biphenyl)-4-yl]-5-methyl-3,4-dihydroxy-2(5H)-furanone, 5-[(4'-fluoro-1,1'-biphenyl)-4-yl]-3,4-dihydroxy-2(5H)-furanone;

5-[(4'-bromo-1,1'-biphenyl)-4-yl]-3,4-dihydroxy-2(5H)-furanone;

5-[(4'-chloro-1,1'-biphenyl)-4-yl]-3,4-dihydroxy-2(5H)-furanone;

5-[(3',4'-dichloro-1,1'-biphenyl)-4-yl]-3,4-dihydroxy-2(5H)-furanone;

5-[(2',4'-dichloro-1,1'-biphenyl)-4-yl]-3,4-dihydroxy-2(5H)-furanone;

5-[(3,4'-dichloro-1,1'-biphenyl)-4-yl]-3,4-dihydroxy-2(5H)-furanone;

5-[(3,4'-dichloro-1,1'-biphenyl)-4-yl]-5-methyl-3,4-dihydroxy-2(5H)-furanone;

5-[(3,4'-dichloro-1,1'-biphenyl)-4-yl]-5-phenyl-3,4-dihydroxy-2(5H)-furanone;

5-[(3,4'-dichloro-1,1'-biphenyl)-4-yl]-5-cyclohexyl-3,4-dihydroxy-2(5H)-furanone;

5-[(3,4'-dichloro-1,1'-biphenyl)-4-yl]-5-(4-nitrophenyl)-3,4-dihydroxy-2(5H)-furanone;

5-[(3-chloro-4'-methyl-1,1'-biphenyl)-4-yl]-3,4-dihydroxy-2(5H)-furanone;

5-[(3-chloro-4'-methyl-1,1'-biphenyl)-4-yl]-5-methyl-3,4-dihydroxy-2(5H)-furanone;

5-[(3-chloro-4'-methyl-1,1'-biphenyl)-4-yl]-5-phenyl-3,4-dihydroxy-2(5H)-furanone;

5-[(3-chloro-4'-methyl-1,1'-biphenyl)-4-yl]-5-cyclohexyl-3,4-dihydroxy-2(5H)-furanone; or 5-[(3-chloro-4'-methyl-1,1'-biphenyl)-4-yl]-5-(4-nitrophenyl)-3,4-dihydroxy-2(5H)-furanone.

The foregoing examples of substituted 5-substituted and 5,5-disubstituted-3,4-dihydroxy-2(5H)-furanones are provided for illustration only and are not intended as a limiting set of compounds that are suitable for the practice of the present invention. The 4-hydroxy analogs of the foregoing compounds are embraced herein as additional, non-limiting examples of the compounds separable by the methods herein.

By way of example, and as will be shown in the Examples below, the enantiomers of the racemic mixtures of the compounds 5-[(1,1'-biphenyl)-4-yl]-3,4-dihydroxy-2(5H)-furanone, and 5-[(4'-chloro-1,1'-biphenyl)-4-yl]-3,4-dihydroxy-2(5H)-furanone may be isolated as follows. Racemic mixtures of these compounds are separated into the pure enantiomers by crystallization with an enantiomerically pure base, preferably (−)-cinchonidine. In specific solvent mixtures, preferably 95% ethanol, the diastereomerically pure salt of the R-enantiomer of the compounds crystallize. The pure R-enantiomer can then be obtained simply by filtration and treatment of the salt with an acid, in preference trifluoracetic acid, followed by precipitation with water, filtration and drying.

Moreover, in some cases the S-enantiomers are equally obtained in pure form by evaporation of the mother liquors, followed by the same treatment of the salt as described above.

The racemic compounds can be separated very simply by resolution with one equivalent of an enantiomerically pure base. This method of resolution, which is well known for carboxylic and sulfonic acids, has been applied herein for the first time to substituted 3,4-dihydroxy-2(5H)-furanones.

In a further aspect of the invention, it has been shown that this separation is even efficient when using only 0.5 equivalent of a chiral base.

As shown by this invention, salts of 5-substituted 4-hydroxy-2(5H)-furanones are stable, at least in the time-scale necessary for the described process, in regard to epimerization of the chiral center (the 5-position of the heterocycle) as also in regard to oxidation in the presence of base. This surprising stability is a necessary condition for a successfull resolution of 5-substituted 4-hydroxy-2(5H)-furanones with chiral bases, and was not apparent previously.

The foregoing examples are merely illustrative of a selection of a racemic mixture of a furanone and the selection of an enantiomerically pure chiral base for performing the separation. The selection of chiral base, the particular enantiomer thereof, and the conditions under which selective precipitation of one of the stereoisomeric salts of one enantiomer of the furanone will be readily determinable by the skilled artisan utilizing the teachings herein.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Methods

Solvents were of commercial quality and were used as received. (−)-Cinchonidine {96%; $[\alpha]^{23}=-109.2°$ (c=1.5; EtOH)} was purchased from Aldrich Chemical and used as such. 5-[(1,1'-biphenyl)-4-yl]-3,4-dihydroxy-2(5H)-furanone and 5-[(4'-chloro-1,1'-biphenyl)-4-yl]-3,4-dihydroxy-2(5H)-furanone were prepared according to Dahn's method [1,2,3,4,5] starting, respectively, from biphenyl-4-carboxaldehyde and 4'-chlorobiphenyl-4-carboxaldehyde [6].

Racemic 5-[(1,1'-biphenyl)-4-yl]-3,4-dihydroxy-2(5H)-furanone (±) 1a: m.p. 194–198° C. (dec.); $^1$H NMR (acetone-$d_6$) δ7.74–7.38 (m, 9H), 5.77 (s, 1H); $^{13}$C NMR (acetone-$d_6$) δ169.9, 153.0, 142.4, 140.8, 135.2, 129.4, 128.4, 128.1, 127.7, 127.4, 118.9, 77.0; Microanalysis: found C 71.46, H 4.50, calculated for $C_{16}H_{12}O_4$ C 71.64, H 4.51.

Racemic 5-[(4'-chloro-1,1'-biphenyl)-4-yl]-3,4-dihydroxy-2(5H)-furanone (±) 1b: m.p. 189–191° C. (dec.); $^1$H NMR (acetone-$d_6$) δ7.6–7.8 (m, 4H), 7.4–7.6 (m, 4H); 5.77 (s, 1H); $^{13}$C NMR (acetone-$d_6$) δ170.0, 153.0, 141.1, 139.7, 135.8, 133.8, 129.6, 129.2, 128.6, 127.8, 119.1, 77.2; Microanalysis: found C 63.68, H 3.72, calculated for $C_{16}H_{11}ClO_4$ C 63.48, H 3.66.

Melting points are measured on a Gallenkamp apparatus and are uncorrected. TLC was performed on silica gel (Macherey Nagel) and developed using cyclohexane/ethyl acetate:½ as eluant. The values of specific rotation were measured on a Perkin-Elmer 341 polarimeter using a 10 cm, 1 ml cell. Elemental analysis were performed by Wolff Laboratories, Clichy, France. $^1$H and $^{13}$C spectra were recorded on a Varian 200 MHz spectrometer; chemical shifts are denoted in δ units (ppm) and the splitting patterns are given in Hz and designated as follows: s (singlet), d (doublet), m (multiplet) and br (broad).

The following scheme illustrates the general object of the invention described herein.

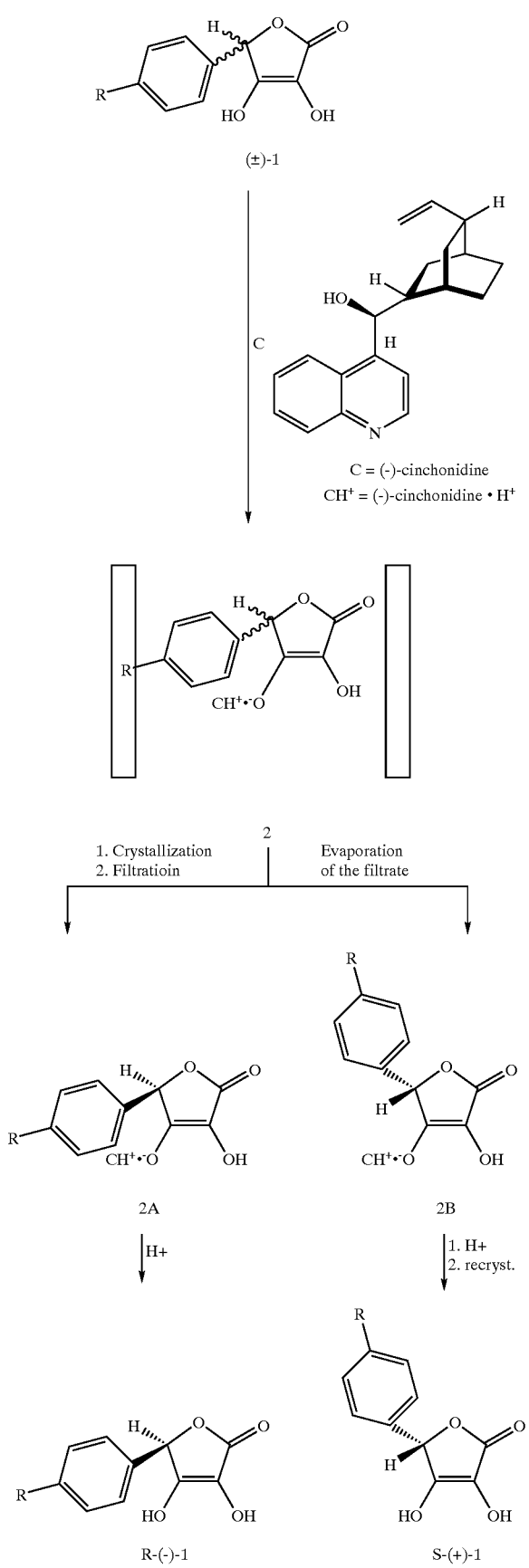

EXAMPLE 2

Resolution of (±) 5-[(1,1'-biphenyl)-4-yl]-3,4-dihydroxy-2(5H)-furanone 1a With Cinchonidine A. Preparation and Separation of Diastereoisomeric Salts 2a-A and 2a-B. In a 50 ml two-necked flask equipped with a thermometer was placed (±) 5-[(1,1'-biphenyl)-4-yl]-3,4-dihydroxy-2(5H)-furanone (2.68 g; 10 mmol) in 95% EtOH (15 ml). To this well stirred suspension was added portionwise, at room temperature, cinchonidine (2.94 g; 10 mmol) for 2 min. An increase of internal temperature (from 20° C. to 28–30° C.) was observed and the initially clear colorless solution crystallized spontaneously at the end of the addition of cinchonidine. The stirring was maintained for one hour and the reaction mixture was then allowed to stand at room temperature overnight (15 h). The voluminous white precipitate was filtered, washed with 95% EtOH (5 ml) and finally dried over $P_2O_5$ at 40° C. to provide pure diastereoisomeric salt 2a-A (2.7 g; 96%).

$^1$H NMR (CDCl$_3$) δ1.15–1.35 (m, 1H); 1.60–1.80 (m, 1H); 1.92–2.15 (m, 3H); 2.55–2.70 (m, 1H); 2.95–3.15 (m, 1H); 3.20–3.50 (m, 3H); 4.35–4.60 (m, 1H); 4.85 (d, 1H, J=5 Hz); 4.93 (d, 1H, J=12.0 Hz); 5.15 (s, 1H); 5.40–5.60 (m, 2H); 6.02 (s, 1H); 7.20–7.55 (m, 11H); 7.62 (d, 1H, J=5.5 Hz); 7.93 (d, 1H, J=9.0 Hz); 8.0 (d, 1H, J=9.5 Hz); 8.75 (d, 1H, J=9.5 Hz).

The mother liquor, obtained by filtration of crystals 2a-A was evaporated to dryness to give the other diastereoisomer 2a-B (2.5 g) as a beige solid residue which was, according to the NMR evaluation test described below, diastereoisomerically pure. However, this crude product contained an impurity whose structure has not been elucidated. No attempt to purify it at this stage was done, the contaminant being removed by crystallization of the liberated acid in the final step.

$^1$H NMR (CDCl$_3$) δ: 1.10–1.35 (m, 1H); 1.50–1.95 (m, 3H); 2.20–2.55 (m, 3H); 2.95–3.10 (m, 3H); 4.15–4.30 (m, 1H); 4.93 (d, 1H, J=5.0 Hz); 4.99 (d, 1H, J=12.2 Hz); 5.34 (s, 1H); 5.40–5.60 (m, 2H); 6.0 (s, 1H); 6.75 (d, 1H, J=8.5 Hz); 6.97 (m, 1H); 7.08 (d,1H, J=8.5 Hz); 7.20–7.60 (m, 8H); 7.65 (d, 1H, J=5.4 Hz); 7.92 (d, 1H, J=9.1 Hz); 7.99 (d, 1H, J=9.1 Hz); 8.85 (d, 1H, J=5.4 Hz).

Diastereoisomeric Excess Evaluation: $^1$H NMR (CDCl$_3$) of the racemic salt (±) 2 showed two clearly separated singlets for the two respective 5-H protons in 2a-A and 2a-B at 5.15 ppm and 5.34 ppm. Examination of $^1$H NMR of salt 2a-A showed a short singlet at 5.15 ppm and no signal at 5.34 ppm, indicating a diastereoisomeric excess higher than 97.6%. Indeed, when adding 0.5 mg of 50% racemic mixture of cinchonidine salt of 1 {prepared by mixing (±) 5-[(1,1'-biphenyl)-4-yl]-3,4-dihydroxy-2(5H)-furanone (536 mg; 2 mmol) with cinchonidine (589 mg; 2 mmol) in EtOH (5 ml) and evaporating the resulting mixture to dryness} to 10 mg of resolved salt 2a-A in CDCl$_3$ (1 ml), the presence of higher field signal at 5.34 ppm pointed out the possibility of detecting 2.4% of the other diastereoisomer.

This method was also applied to determine the diastereoisomeric purity in other described examples.

B. Isolation of Pure R(–)-5-[(1,1'-biphenyl)-4-yl]-3,4-dihydroxy-2(5H)-furanone (R)-1a To a suspension of compound 2a-A (1.0 g; 1.78 mmol) in methanol (10 ml) cooled to 5–10° C., was added dropwise 99% trifluoroacetic acid (5 ml; 65 mmol) for 5 min. At the end of the addition, the reaction mixture was clear. The cooling bath was removed and stirring was maintained for 30 min. Addition of water (50 ml) induced precipitation of product. Subsequent filtration, washing with water (10 ml) and drying over $P_2O_5$ at 50° C. provided enantiomerically pure R-(−)-5-[(1,1'-biphenyl)-4-yl]-3,4-dihydroxy-2(5H)-furanone 1a as a colorless powder (0.44 g; 92%).

TLC and $^1$H NMR analysis were performed here to confirm the absence of traces of cinchonidine in the final product.

$[\alpha]^{20}$=−158° (c=0.665; EtOH); lit.[8], $[\alpha]^{22}$=−154° (c=0.13; EtOH)

C. Isolation of Pure S-(+)-5-[(1,1'-biphenyl)-4-yl]-3,4-dihydroxy-2(5H)-furanone 1a According to the acidic liberation of cinchonidine salt described above for compound (−) 1a, crude compound (+) 1a (0.35 g; 73%) was obtained as a pale yellow solid, starting from cinchonidine salt (±) 2a-B (1.0 g; 1.78 mmol). An unknown contaminant present in this product was removed by crystallization in ethyl acetate (10 ml) which afforded pure enantiomerically (+) 1a (0.19 g; 40%) as a colorless solid.

$[\alpha]^{20}$=+158° (c=0.57; EtOH); lit.[7], $[\alpha]^{22}$=+145° (c=0.11; EtOH).

EXAMPLE 3

Resolution of (±) 5-[(4'-chloro-1,1'-biphenyl)-4-yl]-3,4-dihydroxy-2(5H)-furanone 1b With Cinchonidine A. Preparation and Resolution of Diastereoisomeric Mixture of 2b-A and 2b-B To a suspension of racemic 1b (0.2 g; 0.66 mmol) in 95% EtOH (1 ml) was added at once under stirring, cinchonidine (0.195 g; 0.66 mmol). The clear solution obtained crystallized spontaneously at the end of addition. Stirring was maintained for one hour before the reaction mixture was allowed to stand overnight (15 h) at room temperature. Filtration, washing with 95% EtOH (1 ml) and drying over $P_2O_5$ at 40° C. provided cinchonidine salt 2b-A (0.15 g; 75%) as a colorless solid.

$^1$H NMR (CDCl$_3$) δ: 1.15–1.35 (m, 1H); 1.65–1.90 (m, 1H); 1.95–2.20 (m, 3H); 2.50–2.70 (m, 1H); 3.0–3.20 (m, 1H); 3.25–3.50 (m, 3H); 4.40–5.15 (m, 1H); 4.93 (d, 1H, J=5.5 Hz); 5.0 (d, 1H, J=12.5 Hz); 5.07 (s, 1H); 5.40–5.60 (m, 2H); 6.04 (s, 1H); 7.20–7.55 (m, 10H); 7.67 (d, 1H, J=5.5 Hz); 7.89 (d, 1H, J=9.3 Hz); 8.02 (d, 1H, J=9.8 Hz); 8.88(d, 1H, J=5.5 Hz).

Evaporation of the mother liquor to dryness provided the other diastereoisomer 2b-B (0.23 g; yield>85%) as a pale yellow solid. As in the case of salt 2a-B, this crude product contained a compound of non-elucidated structure and was not purified at this stage.

$^1$H NMR (CDCl$_3$) δ: 1.15–1.4. (m, 1H); 1.60–1.85 (m, 1H); 1.92–2.20 (m, 3H); 2.55–2.70 (m, 1H); 3.05–3.25 (m, 1H); 3.30–3.50 (m, 3H); 4.40–5.15 (m, 1H); 4.95 (d, 1H, J=5.4 Hz); 5.04 (d, 1H, J=12.4 Hz); 5.29 (s, 1H); 5.32–5.60 (m, 2H); 5.8 (s, 1H); 6.32 (d, 1H, J=8.0 Hz); 6.61 (d, 1H, J=8.5 Hz); 6.93 (d, 1H, J=8.0 Hz); 7.11 (d, 1H, J=8.5 Hz); 7.20–7.50 (m, 6H); 7.60 (d, 1H, J=5.5 Hz); 7.79 (d, 1H, J=9.1 Hz); 7.88 (d, 1H, J=9.5 Hz); 8.80(d, 1H, J=5.5 Hz).

B. Isolation of R-(−)-5-[(4'-chloro-1,1'-biphenyl)-4-yl]-3,4-dihydroxy-2(5H)-furanone 1b According to the general procedure described for compound (−)-1a, compound (−)-1b (70 mg; 92%) was isolated as a colorless solid, starting from cinchonidine salt 2b-B (100 mg; 0.25 mmol). $[\alpha]^{20}$=−156° (c=0.45; EtOH).

EXAMPLE 4

Resolution of (±) 5-[(1,1'-biphenyl)-4-yl]-3,4-dihydroxy-2(5H)-furanone 1a With Cinchonidine (0.5 eq.)

A. Preparation and Separation of Diastereoisomeric Salts 2a-A and 2a-B

To a suspension of racemic 1a (2.68 g; 10 mmol) in 95% EtOH (30 ml) was added portionwise under stirring for 3 min, cinchonidine (1.47 g; 5 mmol). The suspension obtained was heated under reflux for 15 min. The clear resulting solution was allowed to stand overnight (15 h) at room temperature, during which time crystallization occured. Filtration, washing with 95% EtOH (5 ml) and drying over $P_2O_5$ at 40° C. provided cinchonidine salt 2a-A (1.2 g; 43%) as a colorless solid.

B. Isolation of Pure R(−)-5-[(1,1'-biphenyl)-4-yl]-3,4-dihydroxy-2(5H)-furanone (R)-1a According to the general procedure described in Example 2 for 5-[(1,1'-biphenyl)-4-yl]-3,4-dihydroxy-2(5H)-furanone, enantiomerically pure R-(−)-5-[(1,1'-biphenyl)-4-yl]-3,4-dihydroxy-2(5H)-furanone 1a was obtained as a colorless powder (89%).

The present invention is not to be limited in scope by the specific embodiments describe herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

1) Dahn, H.; Lawendel, J. S.; Hoegger, E. F.; Schenker, E. Helv. Chim. Acta, 1954, 37, 1309–1318.
2) Dahn, H.; Lawendel, J. S. Helv. Chim. Acta, 1954, 37, 1318–1327.
3) Dahn, H.; Lawendel, J. S.; Fischer, R.; Schenker, E. Experientia, 1954, 10, 245–246.
4) Dahn, H.; Hauth, H. Helv. Chim. Acta, 1956, 39, 1366–1370.
5) Hopper, A. T.; Blokhin, A. V.; Venhodhar, K. R.; Ziemn, J.; Witiak, D. T. Proceedings, XIVth International Symposium on Medicinal Chemistry, 1997, 149–162.
6) Link, P. A. J.; van der Plas, H. C.; Muller, F. Heterocyclic Chem., 1985, 22, 873–878.
7) Hopper, A. T.; Witiak, D. T. J. Org. Chem., 1995, 60, 3334–3341.

What is claimed is:

1. A method for the separation of a racemic mixture of a 5-substituted 4-hydroxy-2(5H)-furanone, comprising the steps of
   (a) reacting in a solvent said racemic mixture with an enantiomerically pure base in an amount sufficient to form a diastereoisomeric salt of said 5-substituted 4-hydroxy-2(5H)-furanone;
   (b) separating a stereoisomeric salt of one enantiomer of said 5-substituted 4-hydroxy-2(5H)-furanone from said solvent.

2. The method of claim 1 wherein said salt is isolated by precipitation.

3. A method for obtaining an enantiomerically pure 5-substituted 4-hydroxy-2(5H)-furanone from a racemic mixture thereof comprising carrying out the separation in accordance with claim 1 and hydrolyzing said isolated stereoisomeric salt of one enantiomer of said 5-substituted 4-hydroxy-2(5H)-furanone.

4. A method for obtaining an enantiomerically pure 5-substituted 4-hydroxy-2(5H)-furanone from a racemic mixture thereof comprising carrying out the separation in accordance with claim 2 and hydrolyzing said precipitated stereoisomeric salt of one enantiomer of said substituted 5-substituted 4-hydroxy-2(5H)-furanone.

5. A method for obtaining an enantiomerically pure 5-substituted 4-hydroxy-2(5H)-furanone from a racemic mixture thereof comprising carrying out the separation in accordance with claim 1, recovering from said solvent a stereoisomeric salt of an enantiomer of said 5-substituted 4-hydroxy-2(5H)-furanone that was not separated, and hydrolyzing said salt.

6. A method for obtaining an enantiomerically pure 5-substituted 4-hydroxy-2(5H)-furanone from a racemic mixture thereof comprising carrying out the separation in accordance with claim 2, recovering from said solvent a stereoisomeric salt of an enantiomer of said 5-substituted 4-hydroxy-2(5H)-furanone that was not separated, and hydrolyzing said salt.

7. The method of claim 1 wherein said 5-substituted 4-hydroxy-2(5H)-furanone is selected from the group consisting of a 5-substituted 4-hydroxy-2(5H)-furanone; a 5,5-disubstituted 4-hydroxy-2(5H)-furanone; a 5-substituted 3,4-dihydroxy-2(5H)-furanone; and a 5,5-disubstituted 3,4-dihydroxy-2(5H)-furanone.

8. The method of claim 1 wherein said enantiomerically pure base is selected from the group consisting of cinchonidine, cinchonine, quinine, quinidine, brucine, strychnine, α-methylbenzylamine, ephedrine, amphetamine, and dehydroabietylamine.

9. A method for the separation of a racemic mixture of a 5-substituted or 5,5-disubstituted 3,4-dihydroxy-2(5H)-furanone, comprising the steps of (a) reacting in a solvent said racemic mixture with an enantiomerically pure base in an amount sufficient to form a diastereoisomeric salt of said 5-substituted or 5,5-disubstituted 3,4-dihydroxy-2(5H)-furanone;

(b) separating a stereoisomeric salt of one enantiomer of said 5-substituted or 5,5-disubstituted 3,4-dihydroxy-2 (5H)-furanone from said solvent.

10. The method of claim 9 wherein said salt is isolated by precipitation.

11. A method for obtaining an enantiomerically pure 5-substituted or 5,5-disubstituted 3,4-dihydroxy-2(5H)-furanone from a racemic mixture thereof comprising carrying out the separation in accordance with claim 9 and hydrolyzing said isolated stereoisomeric salt of one enantiomer of said 5-substituted or 5,5-disubstituted 3,4-dihydroxy-2(5H)-furanone.

12. A method for obtaining an enantiomerically pure 5-substituted or 5,5-disubstituted 3,4-dihydroxy-2(5H)-furanone from a racemic mixture thereof comprising carrying out the separation in accordance with claim 10 and hydrolyzing said precipitated stereoisomeric salt of one enantiomer of said 5-substituted or 5,5-disubstituted 3,4-dihydroxy-2(5H)-furanone.

13. A method for obtaining an enantiomerically pure 5-substituted or 5,5-disubstituted 3,4-dihydroxy-2(5H)-furanone from a racemic mixture thereof comprising carrying out the separation in accordance with claim 9, recovering from said solvent a stereoisomeric salt of an enantiomer of said 5-substituted or 5,5-disubstituted 3,4-dihydroxy-2(5H)-furanone that was not separated, and hydrolyzing said salt.

14. A method for obtaining an enantiomerically pure 5-substituted or 5,5-disubstituted 3,4-dihydroxy-2(5H)-furanone from a racemic mixture thereof comprising carrying out the separation in accordance with claim 10, recovering from said solvent a stereoisomeric salt of an enantiomer of said 5-substituted or 5,5-disubstituted 3,4-dihydroxy-2(5H)-furanone that was not separated, and hydrolyzing said salt.

15. The method of claim 9 wherein said enantiomerically pure base is selected from the group consisting of cinchonidine, cinchonine, quinine, quinidine, brucine, strychnine, α-methylbenzylamine, ephedrine, amphetamine, and dehydroabietylamine.

* * * * *